United States Patent
Strobel et al.

(10) Patent No.: US 6,911,338 B2
(45) Date of Patent: Jun. 28, 2005

(54) ENDOPHYTIC FUNGI AND METHODS OF USE

(76) Inventors: Gary Strobel, 2107 Fairway Dr., Bozeman, MT (US) 59715; Denise C. Manker, 3037 Prado La., Davis, CA (US) 95616; Julien Mercier, 1719 McGee Ave., Berkeley, CA (US) 94703

( * ) Notice: Subject to any disclaimer, the term of this patent is extended or adjusted under 35 U.S.C. 154(b) by 60 days.

(21) Appl. No.: 10/121,740

(22) Filed: Apr. 11, 2002

(65) Prior Publication Data

US 2003/0186425 A1 Oct. 2, 2003

Related U.S. Application Data

(60) Provisional application No. 60/363,072, filed on Mar. 11, 2002, and provisional application No. 60/283,902, filed on Apr. 16, 2001.

(51) Int. Cl.$^7$ ................................................. C12N 1/14
(52) U.S. Cl. ................... 435/254.1; 424/93.5; 504/117; 435/262.5; 435/34
(58) Field of Search .......................... 435/254.1, 262.5, 435/34; 424/93.5; 504/117

(56) References Cited

U.S. PATENT DOCUMENTS

| | | |
|---|---|---|
| 4,954,497 A | 9/1990 | Kamikado et al. |
| 5,270,340 A | 12/1993 | Kunisch et al. |
| 5,612,338 A | 3/1997 | Trah |
| 6,310,005 B1 | 10/2001 | Assmann et al. |

OTHER PUBLICATIONS

Strobel et al., Microbiology, 147:2943–2950, 2001.*

Worapong, et al., Mycotaxon. 81:463–475, 2001.*

* cited by examiner

*Primary Examiner*—Irene Marx
(74) *Attorney, Agent, or Firm*—McDonough Holland & Allen PC; Michelle L. Samonek

(57) ABSTRACT

This invention provides a novel endophytic fungus, *Muscodor*, that produces a mixture of volatile antibiotics with activity on specific plant pathogens, bacteria, nematodes and insects. Also provided is a method for treating or protecting plants, soil and seeds from microbial infections comprising applying an effective amount of a volatile antibiotic producing *Muscodor* sp. The invention also relates to fungicidal, bactericidal, insecticidal and nematicidal compositions comprising this novel *Muscodor* strain and the antibiotics and metabolites produced by this strain either alone, or in combination with other chemical and biological pesticides. Also provided is a method for identifying and isolating related gas producing fungi.

8 Claims, No Drawings

SEQUENCE LISTING

<160> NUMBER OF SEQ ID NOS: 4

<210> SEQ ID NO 1
<211> LENGTH: 2089
<212> TYPE: DNA
<213> ORGANISM: Muscodor albus

<400> SEQUENCE: 1

```
ccggttgatc ctgccagtag tcatatgctt gtctcaaaga ttaagccatg catgtctaag      60
tataagcaat tatacagcga aactgcgaat ggctcattaa atcagttatc gtttatttga     120
tagtacctta ctacttggat aaccgtggta attctagagc taatacatgc taaaaatccc     180
gactcacgga gggatgtatt tattagatta aaaaccaatg cccctcgggg ctttctggtg     240
attcataata acttcacgaa tcgcatggcc ttgcgccggc gatggttcat tcaaatttct     300
gccctatcaa ctttcgatgg cagggtcttg gcctgccatg gttacaacgg gtaacggagg     360
gttagggctc gaccccggag aaggagcctg agaaacggct actacatcca aggaaggcag     420
caggcgcgca aattacccaa tcccgacacg gggaggtagt gacaataaat actgatacag     480
ggctcttttg ggtcttgtaa ttggaatgag tacaatttaa atcccttaac gaggaacaat     540
tggagggcaa gtctggtgcc agcagccgcg gtaattccag ctccaatagc gtatattaaa     600
gttgttgcag ttaaaaagct cgtagttgaa ccttgggcct ggctggccgg tccgcctcac     660
cgcgtgcact ggttcggccg ggcctttccc tctggggagc cccatgcctt tcattaggtg     720
tggtggggaa ccaggacttt tactgtgaaa aaattagagt gttcaaagca ggcctatgct     780
cgaatacatc agcatggaat aatagaatag gacgtgtggt tctattttgt tggtttctag     840
gaccgccgta atgattaata gggacagtcg ggggtgtcag tattcaattg tcagaggtga     900
aattcttgga tttattgaag actaactact gcgaaagcat tcaccaagga tgttttcatt     960
aatcaggaac gaaagttagg ggatcgaaga cgatcagata ccgtcgtagt cttaaccata    1020
aactatgccg actagggatc gggcggtgtt atttttttgac ccgctcggca ccttacgaga    1080
aatcaaagtc tttgggttct gggggagta tggtcgcaag gctgaaactt aaagaaattg    1140
acggaagggc accaccagga gttaaccagc gttacattcg tcgcactctg ctccaaaaag    1200
taggcctgta gaaggctcgg tggcttgctg ataactacta gtctcctgta atggaggcga    1260
cacccttaaa gtgcgggac atcctgttaa aagtctagac gccggacctg gctcggaaac    1320
gagtccaggg cgccagatta accatctggg ttggctaata agtgctagac ttgggactat    1380
```

```
ccgcagccaa acacctgagc tgctagcagt acggtggagg ttcagagact tgacaggggt   1440
gggtgagcag tgttcgcttg cttaagataa agtccgggga cgcatgaaaa tgcagtccaa   1500
ctgtaataac ttacaaccgt aataacggga gcctgcggct taatttgact caacacgggg   1560
aaactcacca ggtccagaca caatgaggat tgacagattg agagctcttt cttgattttg   1620
tgggtggtgg tgcatggccg ttcttagttg gtggagtgat ttgtctgctt aattgcgata   1680
acgaacgaga ccttaacctg ctaaatagcc cctattgctt tggcagtagg ctggcttctt   1740
agagggacta tccgctcaag cggatggaag tttgaggcaa taacaggtct gtgatgccct   1800
tagatgttct gggccgcacg cgcgttacac tgacaggggc agcgagtact ccttagcag    1860 agatgcttgg gtaatcttgt taaaccctgt cgtgctgggg atagagcatt gcaattattg   1920
ctcttcaacg aggaattcct agtaagcgta agtcatcaac ttgcgttgat tacgtccctg   1980 cccctttgtac acaccgcccg tcgctactac cgattgaatg gctcagtgag gctttcggac  2040
tggcccaggg gagtcggcaa cgacacccca gggccggaaa gttatccaa               2089
```

<210> SEQ ID NO 2
<211> LENGTH: 652
<212> TYPE: DNA
<213> ORGANISM: Muscodor albus

<400> SEQUENCE: 2

```
tggaagtaaa agtcgtaaca aggtctccgt tggtgaacca gcggagggat cattacagag    60
ttttccaaac tcccaacccct atgtgaactt acctttgttg cttcggcggc ggaggctacc  120 ctataggga taccacatag tggttaccct gtagtcccag gtgctagatc gtgctcaacg    180
tcttatcgtc tacgactagc tacccggtgg ccctccccgc cggcggccaa ctaaactctg   240
tttttatggc attctgaatt ataaacttaa taagttaaaa ctttcaacaa cggatctctt   300
ggttctggca tcgatgaaga acgcagcgaa atgcgataag taatgtgaat tgcagaattc   360
agtgaatcat cgaatctttg aacgcacatt gcgcccatta gcattctagt gggcatgcct   420
gttcgagcgt catttcacca cttaagccct gttgcttagc gttgggagcc tacggcactg   480
cccgtagctc cctaaagtga ttggcggagt tggttctcac tctaggcgta gtaaatctat   540
ctcgcctctg tagtggttcc ggcccctgcc gtaaaacccc ctatatcaaa ggttgacctc   600
ggatcaggta ggaatacccg ctgaacttaa gcatatcaat aagccgggag ga           652
```

<210> SEQ ID NO 3
<211> LENGTH: 2055
<212> TYPE: DNA
<213> ORGANISM: Muscodor roseus

<400> SEQUENCE: 3

```
ccagtagtca tatgcttgtc tcaaagatta agccatgcat gtctaagtat aagcaattat    60
acagcgaaac tgcgaatggc tcattaaatc agttatcgtt tatttgatag taccttacta   120
cttggataac cgtggtaatt ctagagctaa tacatgctaa aaatcccgac tcacggaggg   180
atgtatttat tagattaaaa accaatgccc ctcggggctt tctggtgatt cataataact   240
tcacgaatcg catggccttg cgccggcgat ggttcattca aatttctgcc ctatcaactt   300
tcgatggcag gtcttggcc tgccatggtt acaacgggta acgagggtt agggctcgac    360 cccggagaag gagcctgaga aacggctact acatccaagg aaggcagcag gcgcgcaaat   420
tacccaatcc cgacacgggg aggtagtgac aataaatact gatacagggc tcttttgggt   480
cttgtaattg gaatgagtac aatttaaatc ccttaacgag gaacaattgg agggcaagtc   540
```

-continued

```
tggtgccagc agccgcggta attccagctc caatagcgta tattaaagtt gttgcagtta     600
aaaagctcgt agttgaacct tgggcctggc tggccggtcc gcctcaccgc gtgcactggt     660
tcggccgggc ctttccctct ggggagcccc atgcctttca ttaggtgtgg tggggaacca     720
ggactttac tgtgaaaaaa ttagagtgtt caaagcaggc ctatgctcga atacatcagc     780
atggaataat agaataggac gtgtggttct attttgttgg tttctaggac cgccgtaatg     840
attaataggg acagtcgggg gtgtcagtat tcaattgtca gaggtgaaat tcttggattt     900
attgaagact aactactgcg aaagcattca ccaaggatgt tttcattaat caggaacgaa     960
agttagggga tcgaagacga ttgccacgag cccgggggct ctggtgcact ggttagccgg    1020
tgtatctggt cgtccataat taggcgcgag cctagttagt ctataacgca ctataggcga    1080
caccgtcaaa ttgcggggac atccttagag cctctaccac acctgcccgc tagaaatagc    1140
gagcagtcgt aacagcgtag gggattggac aatccgcagc caaatccgta ccctgagagg    1200
gctacccggg acttccgggt ggcactccgg ccaggatgca gttcacagac tagacgtcgg    1260
tgggggagta ctccttaaga tatagtcgag ccgccctaga aatggggcgt gatagaagca    1320
gataccgtcg tagtcttaac cataaactat gccgactagg gatcgggcgg tgttattttt    1380
tgacccgctc ggcaccttac gagaaatcaa agtctttggg ttctgggggg agtatggtcg    1440
caaggctgaa acttaaagaa attgacggaa gggcaccacc aggagtggag cctgcggctt    1500
aatttgactc aacacgggga aactcaccag gtccagacac aatgaggatt gacagattga    1560
gagctctttc ttgattttgt gggtggtggt gcatggccgt tcttagttgg tggagtgatt    1620
tgtctgctta attgcgataa cgaacgagac cttaacctgc taaatagccc ctattgcttt    1680
ggcagtaggc tggcttctta gagggactat ccgctcaagc ggatggaagt ttgaggcaat    1740
aacaggtctg tgatgccctt agatgttctg ggccgcacgc gcgttacact gacaggggca    1800
gcgagtactt ccttagcaga gatgcttggg taatcttgtt aaaccctgtc gtgctgggga    1860
tagagcattg caattattgc tcttcaacga ggaattccta gtaagcgtaa gtcatcaact    1920
tgcgttgatt acgtccctgc cctttgtaca caccgcccgt cgctactacc gattgaatgg    1980
ctcagtgagg ctttcggact ggcccagggg agtcggcaac gacacccag ggccggaaag    2040
ttatccaaat cggtc                                                    2055
```

<210> SEQ ID NO 4
<211> LENGTH: 650
<212> TYPE: DNA
<213> ORGANISM: Muscodor roseus

<400> SEQUENCE: 4

```
tggaagtaaa agtcgtaaca aggtctccgt tggtgaacca gcggagggat cattacagag      60
ttttctaaac tcccaaccct atgtgaactt acctttgttg cttcggcggc ggaggctacc     120
ctataggga taccacatag tggttaccct gtagtcccag atgctagatc gtgctcaacg     180
tcttatcgtc tacgactagc tacccggtgg ccctccccgc cggcggccaa ctaaactctg     240
tttttatggc attctgaatt ataaacttaa taagttaaaa ctttcaacaa cggatctctt     300
ggttctggca tcgatgaaga acgcagcgaa atgcgataag taatgtgaat tgcagaattc     360
agtgaatcat cgaatctttg aacgcacatt gcgcccatta gcattctagt gggcatgcct     420
gttcgagcgt catttaccac ttaagccctg ttgcttagcg ttgggagcct acggcactgc     480
ccgtagctcc ctaaagtgat tggcggagtt ggttctcact ctaggcgtag taaatctatc     540
```

| | | | | | |
|---|---|---|---|---|---|
| tcgcctctgt | agtggttccg | gcccctgccg | taaaaccccc | tatatcaaag | gttgacctcg | 600
| gatcaggtag | gaatacccgc | tgaacttaag | catatcaata | agccggagga | | 650

ENDOPHYTIC FUNGI AND METHODS OF USE

CROSS-REFERENCE TO RELATED APPLICATIONS

This application claims the benefit under 35 U.S.C. § 119(e) of U.S. Provisional Application Nos. 60/283,902 and 60/363,072, filed Apr. 16, 2001 and Mar. 11, 2002, respectively. The contents of these applications are hereby incorporated by reference into the present disclosure.

FIELD OF THE INVENTION

The present invention relates to the isolation of novel fungi that produce volatile antibiotics. The volatile compounds have biological activity against plant and human pathogenic fungi and bacteria, insects and nematodes.

BACKGROUND OF THE INVENTION

Throughout this application, various articles and books are referenced by authorship and date. The full bibliographic citation for each publication can be found at the end of the specification, immediately preceding the claims.

It is well recognized that fungi produce antibiotics that are useful in the treatment of diseases, in industrial applications and as pesticides, e.g., penicillin, cephalosporins, tetracyclin, and cyclosporins, none of which are volatile. Many fungal species are known to emit low concentrations of gaseous substances, especially ones that have distinctive obnoxious odors, and this has prompted chemical analyses of the fungal volatiles (Bjurman et al., 1992). Some of these volatile substances are common to many fungi, whereas others seem to be unique for one species (Schnurer et al., 1999; Rapior et al., 2000). Dennis & Webster (1971) reported that certain *Trichoderma* spp. produced volatile antibiotics that inhibited the growth of such test fungi as *Rhizoctonia solani, Pythium ultimum* and *Fusarium oxysporum*. No lethality to any of the test fungi were reported by these authors and comprehensive chemical analyses of the volatile components of the fungal cultures was not performed, although acetaldehyde was suggested as one of the volatiles. Thus, in spite of some attention being given to the volatile compounds of fungal cultures over the years, no lethal mixture of volatile antimicrobials produced by fungi have been reported.

It is also well known that various microorganisms exhibit biological activity so as to be useful to control plant diseases. Although progress has been made in the field of identifying and developing biological pesticides for controlling various plant diseases of agronomic and horticultural importance, most of the pesticides in use are still synthetic compounds. Many of these chemical fungicides are classified as carcinogens by the EPA and are toxic to wildlife and other non-target species. For example, methyl bromide is widely used as a soil fumigant and to treat postharvest microbial infections. Due to its high toxicity to humans and animals and deleterious effect on the atmosphere, the use of methyl bromide will soon be eliminated and there is a great need to find safer replacements for this and other synthetic pesticides.

This invention satisfies this need and provides related advantages as well.

DETAILED DESCRIPTION OF THE INVENTION

Novel endophytic fungi including *Muscodor albus* and *Muscodor roseus* are provided that produce a mixture of volatile antibiotics with activity against fungi, bacteria, insects and nematodes. In one aspect, the *Muscodor* is identified using the information provided herein, including, but not limited to partial genomic sequences set forth in SEQ ID NOs: 1 to 4. Strains of *Muscodor albus* and *Muscodor roseus* were deposited on Feb. 1, 2002 in the Agricultural Research Culture Collection located at 1815 N. University Street Peoria, Ill. 61604 U.S.A. (NRRL) in accordance with the Budapest Treaty on the International Recognition of the Deposit of Microorganisms for the Purpose of Patent Procedure and the Regulations thereunder (Budapest Treaty). The strains were assigned the following Accession Numbers:

*Muscodor albus* 620—Accession Number NRRL 30547
*Muscodor roseus* A3-5—Accession Number NRRL 30548

The strains have been deposited under conditions that assure that access to the cultures will be available during the pendency of this application. However, it should be understood that the availability of a deposit does not constitute a license to practice the subject invention in derogation of patent rights granted by governmental action.

Compositions containing the fungi and/or the volatile compounds are also provided. The compositions are useful to treat soil and to protect plants, seed, grain, and fruit from pathogenic fungi and bacteria. The compositions also are useful to protect postharvest food against bacterial and fungal infections. The compositions are further useful for treating human or animal waste and for treating and/or preventing toxic mold infestations of buildings and building materials such as wood. Methods of treating and protecting soil, plants, seed, grain, waste products, building materials and postharvest food products against bacterial, insecticidal, nematicidal and fungal infections are further provided by this invention.

BRIEF DESCRIPTION OF THE TABLES

Table 1 shows the effects of the volatile compounds of *M. albus* and an artificial mixture of *M. albus* compounds on a group of test microbes. After exposure to *M. albus* gases, the test microbe was evaluated for its viability after removal from the gases. The artificial atmosphere consisted of the compounds identified after analysis of the *M. albus* gases. The microbial growth in the artificial atmosphere was measured after exposure to the artificial mixture of compounds at 3.2–90 $\mu$l/50 cc in order to obtain $IC_{50}$'s. The % growth over the control and viability were measured after exposure to 60 $\mu$l/50 cc. Viability was determined after the removal of the compounds at 3 days.

Table 2 shows the average number of broccoli seedlings per pot one week after planting (means±standard deviation) using vermiculite. Pots were planted immediately without an incubation period.

Table 3 shows the results of an experiment determining the ability of *Muscodor albus* to control blue mold of apple.

Table 4 shows the results of GC/MS analysis of the volatile compounds produced by *M. albus*. Several minor peaks and the breakthrough peak were omitted from the total analysis since they represent only 1% of the total area. Compounds found in the control PDA plate are not included in this table.

Table 5 shows the results of an assay to determine the inhibitory influence of each class of volatile compounds. This is expressed as the % of the test microbe growth as compared to a control not in the presence of the test compounds. The compounds were tested for a 2 day exposure at the relative concentrations that they occur in *M. albus* at the optimum test concentration 60 $\mu$l/50 CC air space or 1.2 $\mu$l/cc.

Table 6 shows *Muscodor albus* volatiles used to treat covered smut infested barley seeds. Sets of untreated and uninfested seeds were used as controls.

MODES FOR CARRYING OUT THE INVENTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which are within the skill of the art. Such techniques are explained fully in the literature. These methods are described in the following publications. See, e.g., Sambrook et al. MOLECULAR CLONING: A LABORATORY MANUAL, $2^{nd}$ edition (1989); CURRENT PROTOCOLS IN MOLECULAR BIOLOGY (F. M. Ausubel et al. eds. (1987)); the series METHODS IN ENZYMOLOGY (Academic Press, Inc.); PCR: A PRACTICAL APPROACH (M. MacPherson et al. IRL Press at Oxford University Press (1991)); and PCR 2: A PRACTICAL APPROACH (M. J. MacPherson, B. D. Hames and G. R. Taylor eds. (1995)).

Definitions

The singular form "a," "an" and "the" include plural references unless the context clearly dictates otherwise. For example, the term "a cell" includes a plurality of cells, including mixtures thereof.

The term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and agriculturally acceptable carriers. "Consisting of" shall mean excluding more than trace elements of other ingredients and substantial method steps for applying the compositions of this invention. Embodiments defined by each of these transition terms are within the scope of this invention.

As used herein, "biological control" is defined as control of a pathogen or insect by the use of a second organism. Known mechanisms of biological control include enteric bacteria that control root rot by out-competing fungi for space on the surface of the root. Bacterial toxins, such as antibiotics, have been used to control pathogens. The toxin can be isolated and applied directly to the plant or the bacterial species may be administered so it produces the toxin in situ.

The term "fungus" or "fungi" includes a wide variety of nucleated spore-bearing organisms that are devoid of chlorophyll. Examples of fungi include yeasts, molds, mildews, rusts, and mushrooms.

The term "bacteria" includes any prokaryotic organism that does not have a distinct nucleus.

"Pesticidal" means the ability of a substance to increase mortality or inhibit the growth rate of plant pests.

"Fungicidal" means the ability of a substance to increase mortality or inhibit the growth rate of fungi.

"Insecticidal" means the ability of a substance to increase mortality or inhibit the growth rate of insects or their larvae.

"Bacterial" means the ability of a substance to increase mortality or inhibit the growth rate of bacteria.

"Nematicidal" means the ability of a substance to increase mortality or inhibit the growth rate of nematodes.

"Antibiotic" includes any substance that is able to kill or inhibit a microorganism. Antibiotics may be produced by a microorganism or by a synthetic process or semisynthetic process. The term, therefore, includes a substance that inhibits or kills fungi for example, cycloheximide or nystatin.

The term "culturing" refers to the propagation of organisms on or in media of various kinds. "Whole broth culture" refers to a liquid culture containing both cells and media. "Supenatant" refers to the liquid broth remaining when cells grown in broth are removed by centrifugation, filtration, sedimentation, or other means well known in the art.

An "effective amount" is an amount sufficient to effect beneficial or desired results. An effective amount can be administered in one or more administrations. In terms of treatment and protection, an "effective amount" is that amount sufficient to ameliorate, stabilize, reverse, slow or delay progression of the target infection or disease states.

"Positive control" means a compound known to have pesticidal activity. "Positive controls" include, but are not limited to commercially available chemical pesticides. The term "negative control" means a compound not known to have pesticidal activity. Examples of negative controls are water or ethyl acetate.

The term "metabolite" or "volatile" refers to any compound, substance or byproduct of a fermentation of a microorganism that has the biological activity. Volatiles in most instances evaporate readily at ambient temperature and pressure.

The term "mutant" refers to a variant of the parental strain as well as methods for obtaining a mutant or variant in which the desired biological activity is similar to that expressed by the parental strain. The "parent strain" is defined herein as the original *Muscodor* strains before mutagenesis. Mutants occur in nature without the intervention of man. They also are obtainable by treatment with or by a variety of methods and compositions known to those of skill in the art. For example, parental strains may be treated with a chemical such as N-methyl-N'-nitro-N-nitrosoguanidine, ethylmethanesulfone, or by irradiation using gamma, x-ray, or UV-irradiation, or by other means well known to those practiced in the art.

A "composition" is intended to mean a combination of active agent and another compound, carrier or composition, inert (for example, a detectable agent or label or liquid carrier) or active, such as an adjuvant. Examples of agricultural carriers are provided below. The fungi can also be formulated as a composition, with a carrier or alternatively, with at least one chemical or biological pesticide.

All numerical designations, e.g., pH, temperature, time, concentration, and molecular weight, including ranges, are approximations which may be varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are well known in the art.

In order to achieve good dispersion and adhesion of compositions within the present invention, it may be advantageous to formulate the whole broth culture, supernatant and/or volatile with components that aid dispersion and adhesion. Suitable formulations will be known to those skilled in the art (wettable powders, granules and the like, or can be microencapsulated in a suitable medium and the like, liquids such as aqueous flowables and aqueous suspensions, volatile compositions and emulsifiable concentrates. Other suitable formulations will be known to those skilled in the art.

A "variant" is a strain having all the identifying characteristics of the strains of this invention and can be identified as having a genome that hybridizes under conditions of high stringency to the genome of the organism, the partial sequence of which has been deposited in the GenBank depository. "Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. Hybridization reactions can be performed under conditions of different "stringency." In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

A variant may also be defined as a strain having a genomic sequence that is greater than 85%, more preferably greater than 90% or more preferably greater than 95% sequence identity to the genome of *M. roseus* or *M. albus*. A polynucleotide or polynucleotide region (or a polypeptide or polypeptide region) has a certain percentage (for example, 80%, 85%, 90%, or 95%) of "sequence identity" to another sequence, which means that, when aligned, that percentage of bases (or amino acids) are the same in comparing the two sequences. This alignment and the percent homology or sequence identity can be determined using software programs known in the art, for example, those described in *Current Protocols in Molecular Biology* (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. These software programs are publicly available through the National Center for Biotechnology (Bethesda, Md.).

Applicants have isolated and characterized a novel fungi named *Muscodor*. Two species of the novel *Muscodor* have also been isolated and characterized, i.e., *Muscodor albus* and *Muscodor roseus*. Partial genomic sequences for *Muscodor albus* are provided in SEQ ID NOS.: 1 and 2 and partial genomic sequences for *Muscodor roseus* (designated A3-5) are provided in SEQ ID NOS. 3 and 4. A partial genomic sequence for *M. roseus* (A10) was also obtained. An isolated culture of *Muscodor albus* has been deposited with the NRRL under Accession No. 30457. An isolated culture of *Muscodor roseus* designated A3-5 has been deposited with the NRRL under Accession No. 30458. Thus, this invention provides an isolated novel fungi designated *Muscodor* and two species thereof, *Muscodor albus* and *Muscodor roseus*, and mutants thereof.

Also provided by this invention are gaseous composition(s) ("volatiles") produced by the isolated *Muscodor* cultures. In one aspect, the volatile composition has the components recited in Table 4. The gaseous compositions can be combined with a suitable dispersing agent or carrier. In another aspect, the compositions optionally contain an effective amount of one or more of a fungicide, an insecticide, a nematicide, an antimicrobial, a bactericide or a food preservative.

Applicants have further identified the components of the volatile byproduct and have synthesized it from commercially available materials. The components of the synthetic volatile are recited in Table 4. It should be understood, although not always explicitly stated that the synthetic composition can be used in the methods described herein as an alternative or as a substitute to the natural gaseous byproduct produced by *Muscodor fungi*.

*Muscodor* gases affect a number of other microbes related to human health issues. It is lethal to the major fungal and bacterial pathogens of humans including *C. albicans* and *A. fumigatus* (Table 1) and *Pseudomonas* sp. It kills bacteria that contaminate food such as *S. aureus* and *E. coli* (Table 1). It has been found to be lethal to *Stachybotrys* sp. (contaminator of homes, and public buildings) and also a number of wood decay fungi.

Thus, the fungi and the gases produced by the fungi are useful to inhibit the growth of or kill an organism selected from the group consisting of a fungus, a bacteria, a microorganism, a nematode and an insect. Using methods well known to those of skill in the art, the fungi or its volatile byproduct is contacted with the organism in an amount effective to kill or inhibit the growth of the organism. Alternatively, the fungi and/or its volatile byproduct can be used to treat human or animal waste, e.g., as a component of a waste water or solid management or treatment. They also are useful to decontaminate human and animal waste, e.g., decrease or remove bacterial and fungal contamination. Yet further, the fungi and/or its volatile byproduct can be used to treat or prevent toxic mold on building materials and in buildings by contacting the building, the building materials, or the spaces between the building materials with an effective amount of the volatile byproduct. For the purpose of illustration only, an effective amount of the volatile byproduct can be used alone or in combination with other fumigants in a room or alternatively, during whole building fumigations.

When used in agricultural applications, the invention provides a method for treating or protecting fruit, seeds, plants or the soil surrounding the plants from an infestation by an organism selected from the group consisting of a fungus, a bacteria, a microorganism, and an insect, by contacting the microorganism with an effective amount of an isolated *Muscodor* culture or its volatile byproduct.

Further provided by this invention is a method for identifying novel *Muscodor* fungi, comprising contacting an effective amount of the fungi to be screened with the volatiles of *Muscodor albus* or *Muscodor roseus* under culturing conditions and selecting the fungi which is resistant to the volatiles of the *Muscodor albus* or *Muscodor roseus* thereby identifying novel *Muscodor* fungi. Further provided are the isolated *Muscodor* fungi selected by this method.

Yet further provided is a method for obtaining a volatile composition by culturing the isolated *Muscodor* of this invention and collecting the volatile composition produced by the growing *Muscodor*.

The following examples are provided to illustrate the invention. These examples are not to be construed as limiting.

EXAMPLES

Example 1

Fungal Isolation

*Muscodor albus*

Several small limbs of a mature *Cinnamomum zeylanicum* tree located 20 miles west of La Ceiba, Honduras, were removed and immediately transported back to Montana State University for processing in the fall of 1997. Small pieces of inner bark, sapwood and outer xylem tissues of the limbs were aseptically removed and placed on Petri plates containing water agar. After incubation for several days, hyphal tips of developing fungi were aseptically removed and placed on potato dextrose agar (PDA). In addition, after 7 days, fungal colonies were transferred to gamma irradiated carnation leaves (0.5×0.5 cm) to encourage spore production. Of several fungi that were isolated the one of great interest, because of its musty odor, was an isolate designated—"620", later identified as *Muscodor albus*.

*Muscodor roseus*

Fungus was isolated from several small limbs of a Fern-Leafed *Grevellia* (*Grevillea pteridifolia*) 12°59'39" South and 132°28'50" East obtained from the Northern Territory of Australia. Small pieces of inner bark, sapwood and outer xylem tissues of some small limbs (0.5 cm dia) were aseptically removed and placed on Petri plates containing water agar (Strobel et al., 1996). After incubation for several days, hyphal tips of developing fungi were aseptically removed and placed on potato dextrose agar (PDA). In addition, after 7 days, fungal colonies were transferred to gamma irradiated carnation leaves (0.5×0.5 cm) and other plant materials to encourage spore production. Of the several fungi that were isolated, the one of greatest interest, because of its musty odor, was an isolate designated—"A3-5."

An additional strain of *Muscodor* was obtained from the small limbs of the Australia Ironwood (*Erythophelum chlorostachys*) at 15°29'29" South and 131°23'12" East. This endophyte was isolated using the volatiles of *M. albus* as a selection tool. Plant material, from which endophytes were to be isolated, were placed in the same agar plate as a rapidly growing two-week old culture of *M. albus*. Then, the only organisms developing from the plant material were the ones resistant to *M. albus*, which are possibly other volatile antibiotic producers or relatives of *M. albus* in the xylariaceous group (Strobel et al., 2001). The most commonly isolated endophytes from this tree were *Pestalotiopsis* spp. and other *Xylaria* spp. It was internally designated "A-10".

Example 2

Fungal Growth and Storage

The fungus was grown on a number of different media including Tryptic Soy Broth Agar (TSBA), Corn Meal Agar (CMA), Malt Agar (MA), Potato Dextrose Agar (PDA), Difco, Laboratories, Detroit, Mich. Also the fungus was inoculated on to Petri plates containing water agar with individual samples of small wood shavings of western white pine (*Pinus monticola*), black walnut (*Juglans nigra*), and maple (*Acer saccharum*) as well as bark pieces of *C. zeylanicum* in order to encourage spore production.

In order to determine how to best store isolate 620, several conditions were tried. The fungus was grown on sterilized Whatmann No. 1 filter paper discs that were placed on to the surface of PDA in Petri Plates. The fungus was inoculated as an agar plug in the middle of the filter paper disc on the PDA plate. The plate was incubated for 14 days at 22° C. The paper disc was then removed and placed in a laminar flow hood under sterile conditions for 1 day, or until the paper with its fungal mycelium was dry. The paper disc was then cut into many pieces and stored under various conditions. Also, agar plugs containing the fungus were placed in sterile distilled water and stored at 4° C.: In another set of test conditions, mycelial pieces growing on agar were placed in 15% glycerol and stored at −70° C. In each test, fungal viability was determined by placing the mycelial fragments on to a PDA plate and examining it for fungal growth after 3–4 days.

In order to determine how to best store *Muscodor roseus* isolates (designated internally as A3-5 and A-10) several conditions were tried. The fungus was grown on sterilized Whatmann No. 1 filter paper discs that were placed on to the surface of PDA in Petri Plates. The fungus was inoculated as an agar plug in the middle of the filter paper disc on the PDA plate. The plate was incubated for 14 days at 22° C. The paper disc was then removed and placed in a laminar flow hood under sterile conditions for 1 day, or until the paper with its fungal mycelium was dry. The paper disc was then cut into many pieces and stored at 23° C., 4° C., 0° C. and −70° C. Also, agar plugs containing the fungus were placed in sterile distilled water and stored at 4° C. In another set of test conditions, mycelial pieces growing on agar were placed in 15% glycerol and stored at −70° C. In each test, fungal viability was determined by placing the mycelial fragments on to a PDA plate and examining it for fungal growth after 3–4 days.

Example 3

Fungal DNA Isolation

For DNA isolation, all fungi were grown in potato dextrose broth (PDA) in 1.5 ml for 18 to 24 h at 23° C. The mycelium was harvested by centrifugation and washed twice with sterile $ddH_2O$. Total genomic DNA was extracted by the methods of Lee and Taylor (1990).

Example 4

Amplification of 18S Ribosomal DNA

Partial nucleotide base pair fragments of the 18S r DNA gene from each fungus was amplified via the polymerase chain reaction (PCR) as a single fragment with the primer UK4F (5' CYGGTTGATCCTGCCRG) and UREV (5'GYTACCTTGACGA ACTT). PCR was performed in a 50 µl reaction vial containing 0.1 µg genomic DNA, 0.4 µM each primer, 0.16 mM four dNTPs and 5µ Taq polymerase (Promega) in a buffer of 10 mM tris-HCl (pH 9.0 at 25° C.), 50 mM KCl, 3 mM $MgCl_2$, 0.1% Triton X-100. Amplification was for 30 cycles (45 s at 94.5° C., 45 s at 53.5° C., 90 at 72.5° C.).

Example 5

Amplification of Internal Transcribed Space Sequences (ITS) and 5.8S rDNA.

The ITS regions of the test fungus was amplified using PCR and the universal ITS primers ITS5 (5'

GGAAGTAAAAGTCGTAACAAGG) and ITS4 (5' TCCTCCGCTTATTGATATGC) (White et al., 1990). PCR was performed in a 50 μl reaction containing 0.1 μg genomic DNA, 0.4 μM each primer, 0.16 mM four dNTPs and 5u Taq polymerase (Promega) in a buffer of 10 mM tris-HCl (pH 9.0 at 25° C.), 50 mM KCl, 3 mM $MgCl_2$, and 0.1% Triton X-100. PCR cycling conditions consisted of denaturation at 94° C. for 1.5 min, annealing at 55° C. for 2.5 min, and extension at 72° C. for 3 min for 40 cycles, with a final extension at 72° C. for 10 min (Willits, 1999). The PCR products were gel purified and desalted using the QuickStep PCR purification kit (Edge Biosystems).

Example 6

Searching and Comparison 18S rDNA and ITS1&2 Sequences

*Muscodor albus*

Both 18S rDNA and ITS 1–2 sequences of *Muscodor albus* were submitted to GenBank with serial numbers AF324337 and AF324336, respectively. These sequences were also were searched or compared with other fungal sequences under BLAST 2.1. and a search of NCBI at the web site www.ncbi.nlm.nih.gov/BLAST. Comparison and alignment sequences were done by using Clustal W version 1.7 (Thomson, J. and Gibson T., 1997), and manually aligned afterward.

Maximum parsimony bootstrap method (Felsenstein, 1985) with heuristic search and maximum parsimonious consensus heuristic search were performed using PAUP* (Swofford, 1999). The bootstrap analysis was set as the following: 100 replications, tree bisection-reconnection branch swapping, and random sequence addition. All characters were weighted equally. Reference taxa were *Taphrinales: Protomyces inouyei* (GenBank serial number D11377), *Taphrina wiesneri* (D12531), *T. deformans* (U00971) and *T. pruni-subcordatae* (AB000957).

*Muscodor roseus*

Both 18S rDNA and ITS1&2 sequences of culture collection "A3-5" were submitted to GenBank with serial number AY034664 and AY034665, respectively. While the 18S r DNA of isolate "A-10" was assigned AYO49023. In addition, both 18S rDNA and ITS1&2 sequences of "A3-5" also were searched or compared with other fungal sequences under BLAST 2.2.1 (Altschul et al., 1997), a search of NCBI at the web site http://www.ncbi.nlm.nih.gov/BLAST. Comparison and alignment sequences were done by using CLUSTALW version 1.7 (Thomson and Gibson, 1997), and manually aligned afterward.

Phylogenetic analysis of the aligned 1708 bp of partial 18S rDNA sequences was performed using the maximum parsimony analysis of the Phylogeny Using Parsimony Analysis (PAUP*) program version 4.0b4a (Swofford, 1999). The number of parsimony-informative characters are 190, and 1448 characters and are constant. The phylogenetic analysis was performed on eighteen taxa, including reference taxa. The reference taxa were Traphinales: *Taphrina wiesneri* (GenBank accession number D12531), *Taphrina deformans* (U00971) and *Taphrina pruni-subcordatae* (AB000957). The remaining fifteen species were *Muscodor albus* (AF324337), *Muscodor roseus* (AY034664), *Xylaria carpophila* (Z49785), *X. curta* (U32417), *X. hypoxylon* (U20378), *X. polymorpha* (AB014043), *Xylaria* sp. (AB014042), *Rosellinia necatrix* (AB014044), *Poronia punctata* (AF064052), *Daldinia concentrica* (U32402), *Hypoxylon fragiforme* (AB014046) and *Hypoxylon atroroseus* (U32411), *Pestalosphaeria hansenii* (AF242846) *Discostroma tricellular* (AF346546) and *Amphisphaeria* sp. (AF346545). The bootstrap analysis was set as the following: 100 replications, tree bisection-reconnection branch swapping, random sequence addition. All characters were weighted equally.

Example 7

Analysis of Antibiotic Volatiles Produced by *Muscodor albus*

A method was devised to analyze the gases in the air space above the *M. albus* mycelium growing in Petri plates. A "Solid Phase Micro Extraction" syringe was used to trap the fungal volatiles. The fiber material (Supelco) was 50/30 divinylbenzene/carburen on polydimethylsiloxane on a stable flex fiber. The syringe was placed through a small hole drilled in the side of the Petri plate and exposed to the vapor phase for 45 min. The syringe was then inserted into a gas chromatograph (Hewlett Packard 5890 Series II Plus) equipped with a mass-selective detector. A 30 m×0.25 mm I.D. ZB Wax capillary column with a film thickness of 0.50 mm was used for the separation of the volatiles. The column was temperature programmed as follows: 25° C. for 2 min followed to 220° C. at 5° C./min. The carrier gas was Helium Ultra High Purity (local distributor) and the initial column head pressure was 50 kPa. The He pressure was ramped with the temperature ramp of the oven to maintain a constant carrier gas flow velocity during the course of the separation. Prior to trapping the volatiles, the fiber was conditioned at 240° C. for 20 minutes under a flow of helium gas. A 30 sec. injection time was used to introduce the sample fiber into the GC. The gas chromatograph was interfaced to a VG 70E-HF double focusing magnetic mass spectrometer operating at a mass resolution of 1500. The MS was scanned at a rate of 0.50 sec. per mass decade over a mass range of 35–360 amu. Data acquisition and data processing was performed on the VG SIOS/OPUS interface and software package. Initial identification of the unknowns produced by *M. albus* was made through library comparison using the NIST database.

Comparable analyses were conducted on Petri plates containing only PDA and the compounds obtained therefrom, mostly styrene, were subtracted from the analyses done on plates containing the fungus. Final identification of 20/28 compounds was done on a comparative basis to authentic standards using the GC/MS methods described herein. However, 8 other compounds composing only approximately 20% of the volatiles have only been tentatively identified on the basis of the NIST data base information and were not included in any of the bioassay tests that employed artificial mixtures of *M. albus* compounds.

As a first approximation, the quantitative analysis of each compound found in fungal cultures is based on its relative peak area obtained after GC-MS analysis. This number was used to prepare artificial atmospheres of the *M. albus* gases in the relative proportions that they occur in culture.

Example 8

Sourcing of Fungal Volatile Compounds

The majority of the compounds produced by *M. albus* were obtained from Aldrich Chem Co., however, valencene was obtained from Fluka Chem Co. and synthetic bulnesene was obtained from Dr. Clayton Heathcock of U.C. Berkeley, Dept of Chemistry and can be synthesized following the procedures of Heathcock and Ratcliffe (1971).

The other esters that were not commercially available were made following some of the acylation procedures as set forth in Hoefle, G. et al., (1978).

Propanoic acid, 2-methyl,3-methylbutyl ester. Isobutyryl chloride (2 ml 19.1 mmol) was slowly added to a 0 C solution of isoamyl alcohol (1 ml, 9.5 mmol), 4-dimethylaminopyridine (583 mg, 4.8 mmol), and pyridine (0.85 ml, 10.5 mmol) in dichloromethane. A precipitate was evident 5 minutes after addition was complete. After stirring 12 h under argon, the reaction was poured into 20 ml of 0.1 N HCl. The layers were separated and the aqueous layer was extracted with 20 ml of methylene chloride. The organic layers were combined and washed with 10 ml of saturated aqueous ammonium chloride then 10 ml of saturated aqueous sodium bicarbonate. The organic layers were dried over magnesium sulfate, filtered, and concentrated in vacuo. Purified by distillation through a 14 mm Vigreaux column (bp 60–62 C, 25 mm). The resulting clear, colorless oil was stirred over Amberlyst 15 to remove any remaining isobutyryl chloride. $^1$H NMR (250 MHz, $CDCl_3$) 4.09 (t, 2H, J 6.7), 2.53 (m, 1H), 1.68 (m, 1H), 1.52 (q, 2H, J 6.5), 1.16 (d, 6H, J 7.0), 0.92 (d, 6H, J 6.5).

Propanoic acid, 2-methyl-ethyl ester. Isobutyryl chloride (2 ml 19.1 mmol) was slowly added to a 0 C solution of ethyl alcohol (0.55 ml, 9.5 mmol), 4-dimethylaminopyridine (583 mg, 4.8 mmol), and pyridine (0.85ml, 10.5 mmol) in dichloromethane. A precipitate was evident 5 minutes after addition was complete. After stirring 12 h under argon, the reaction was poured into 20 ml of 0.1 N HCl. The layers were separated and the aqueous layer was extracted with 20 ml of methylene chloride. The organic layers were combined and washed with 10 ml of saturated aqueous ammonium chloride then 10 ml of saturated aqueous sodium bicarbonate. The organic layers were dried over magnesium sulfate, filtered, and concentrated in vacuo. Purified by distillation through a 14 mm Vigreaux column (bp 102 C). $^1$H (300 MHz, $CDCl_3$) 4.12 (q, 2H, J 7.2), 2.52 (m, 1H), 1.25 (t, 3H, J 6.9), 1.16 (d, 6H, J 7.2).

1-Butanol, 3 methyl, acetate. Under an atmosphere of argon, acetyl chloride (6.5 ml, 91.8 mmol) was added dropwise to a 0° C. solution of isoamyl alcohol (5 ml, 45.9 mmol), N, N-dimethylpyridine (2.8 g, 23 mmol), and anhydrous pyridine (4.1 ml, 50.5 mol) in dichloromethane (92 ml). The reaction mixture was poured into 100 ml of 0.1 N HCl, and the resulting layers were separated. The organic layer was washed with 50 ml of saturated aqueous ammonium chloride then dried over magnesium sulfate. The organic layer was filtered and concentrated in vacuo to a clear oil. The resulting oil was purified by distillation (bp 134–136° C.) to give isoamyl acetate. $^1$H NMR (300 MHz, $CDCl_3$) 4.08 (t, 2H, J 6.9), 2.03 (s, 3H), 1.68 (m, 1H), 1.51 (q, 2H, J 6.9), 0.92 (d, 2H, J 6.6).

Example 9

Inhibition of Fungal and Human Pathogens by Volatiles in in Vitro Petri Plate Assays A strip of agar was removed from the middle of PDA plates, creating two approximately equal and separate sections where microorganisms could grow, as described by Strobel et al., 2001. One agar plug of *M. albus* culture was placed on one section and grown for 10 days with the plates enclosed in a plastic bag. After ten days, the other section was inoculated with various fungal pathogens, with sectioned plates without *M. albus* serving as control. There were three plates for each treatment. *Penicillium expansum,* *Monilinia fructicola, Candida albicans* and bacteria were applied as a spore/cell suspension, while the other pathogens were applied as a single 3 or 6 mm mycelial plug in each plate. Pathogen growth, measured by colony diameter, was evaluated after 3 days. Reisolation of pathogens, to evaluate their viability, was attempted at the end of the experiments by lifting the agar in the inoculated area and transferring it to fresh PDA plates.

The relative ability of the authenticated volatile *M. albus* compounds to inhibit and kill test organisms is also shown in Table 1. Test solutions were prepared by placing compounds in vials in the relative proportions that they occurred in the gas phase of *M. albus* cultures. The test mixture was placed in a presterilized microcup (4×6 mm) located in the center of a Petri plate containing PDA. When not in use, the mixture was stored at 0° C. The test organisms, freshly growing and excised on 3 $mm^3$ agar blocks (at least 3 agar blocks per test fungus), were placed 2–3 cm from the microcup and the plate wrapped with two layers of parafilm. Measurements were made on mycelial growth from the edge of the agar blocks after a given time period. However, in the case of bacteria and *Candida albicans* they were streaked on the test side of the PDA plate and checked for new visible growth and viability by restreaking from the original area of the agar plate that had been inoculated. Appropriate controls were also set up in which no test solution was placed into the microcup. Tests on 3.2–90 µl of the artificial mixture per 50 CC of air space above the PDA plate were done on 3 replicates in order to obtain $IC_{50}$ data for each test organism. Individual classes of compounds were also tested in the relative amounts in which they occur at the optimum concentration of the entire mixture which is 60 µl of test mixture per 50 CC of air space above the culture in a standard Petri plate. For instance, the esters represent 44% of the mixture of the identified volatiles and were tested at 26.4 µl/50 CC air space and the same procedure was used for each of the other classes of compounds that were identified. Finally, each individual compound, especially among the esters, was tested at the concentration or relative percentage in which it occurs in 60 µl. Viability of the test microbes was made by aseptically removing the small agar block and placing it on a PDA plate and observing growth after 1–3 days.

None of the pathogens, except *F. solani* and *F. oxysporum lycopersici*, grew in the presence of *M. albus* (Table 1) and their growth was inhibited. Both of these pathogens survived in the presence of *M. albus*, when transferred to fresh plates three days later. Also the volatiles of *M. albus* did not kill *M. albus* itself or its close relative *Xylaria* sp., although they did inhibit the growth of *Xylaria* sp. (Table 1).

Example 10

Testing of Classes of Volatile Compounds and Individual Volatile Components in in vitro Assays Individual classes of compounds in the natural volatiles of *M. albus* were evaluated in order to determine the relative biological activity of each. Each class of compounds, in the relative proportions that they occur, was tested at the level of the percentages that they occur in the total 60 µl/50 CC (1.2 µl/CC) (Table 5). This was done with a selected group of 7 test fungi. Each group of compounds possessed some inhibitory activity against the test organisms (Table 5). However, on a comparative basis the esters had more inhibitory activity than any other group of compounds (Table 5).

Each compound in the class of esters was individually evaluated. When a comparable test on each ester was conducted as per the conditions in Table 5, 1-butanol, 3-methyl, acetate, almost completely mimicked the results of all esters as in Table 5. It represented 62% of all of the identified combined esters and was therefore tested at the level of 0.32 μl/CC. Additionally, minimal inhibitory bioactivity was displayed by propionic acid, 2-methyl, 3-methylbutyl ester and little or no activity was noted on the part of the other esters. Although the esters, and the 1-butanol, 3 methyl-acetate had inhibitory activity in the bioassay tests, under no conditions in any test, was death of any test fungus observed under the standard 3 day exposure period (Table 5). This is a significant observation, since the death of test organisms was noted in both the complete artificial atmosphere and in the natural Petri plate atmosphere of *M. albus*. The result strongly suggests that an additive or synergistic mechanism is operational in the case of the *M. albus* volatiles. Thus, while each class of compounds possesses more or less inhibitory activity, a complete mixture of the ingredients is needed to bring about death of the test fungi and bacterium (Table 1).

Based on the fact that the volatiles of *M. albus* can inhibit and kill *E. coli* (Table 1) experiments were done using *M. albus* to determine if its gases can inhibit and kill the microflora found in human and animal wastes such as *E. coli* and other fecal microbes. These microbes commonly are the cause of dysentery and other diseases during times of major crises including natural disasters, and wars. Conceivably, *M. albus* could be developed and used for field applications to decontaminate human and animal wastes. Thus, according to our experiments, a two week old colony of *M. albus* growing on a half side of a Petri plate containing PDA was prepared. Then on the separated other half plate was streaked (using standard microbiological methods) solid human waste. A control plate was set up in which no colony of *M. albus* was present. After two days, of incubation at 23° C., there were significantly more bacterial and fungal colonies growing in the control plate than the plate with *M. albus*. In a comparable experiment, *M. albus* was incubated solely in liquid human waste (urine) and total bacterial growth was precluded as contrasted to a control (without the *M. albus*) in which bacterial growth flourished.

Example 11

Activity of *Muscodor albus* Against the Soil Pathogen *Rhizoctonia solani* in vivo For these experiments, the growing medium is first infested with *R. solani* by adding one culture on a PDA plate to 1L of growing medium (vermiculite). This rate allows near 100% seedling mortality with low variability among pots. *Muscodor albus* in various forms is then added to the growing medium, which is then placed in 3 inch plastic pots. The pots are planted with approximately 70 seeds of broccoli, placed in a tray and watered from the bottom. The seedlings are counted after approximately one week. Controls consist of *R. solani* only, *Muscodor albus* only and plain growing medium. Depending on the experiment, there are 3 or 4 pots per treatment, arranged in a completely randomized design.

A 10 day-old liquid culture of PDB was homogenized for a few seconds in a blender and incorporated at a rate of 50 or 200 ml per L of vermiculite. The solid agar culture treatment was done as described above, with 2 plates of 2 week-old culture per L. The pots were sown immediately after filling. The effect of sealing the volatiles in the pots was also investigated: for each treatment, a plastic bag was sealed over 3 pots with a rubber band while 3 other pots were left uncovered. The bags were removed after 3 days. Results show that liquid culture applied at the higher rate (200 ml/L of vermiculite) was as effective in preventing damping off as solid *Muscodor* cultures on PDA (Table 2). The effect of *Muscodor* application appears to be immediate, as normal emergence rates were obtained with these treatments, even though there was no incubation period before planting. The low rate of liquid culture caused some reduction in damping off, but was not as effective. Sealing the volatiles in the pot with a plastic bag did not improve efficacy (Table 2).

Example 12

Activity of *Muscodor albus* as a Postharvest Treatment of Infested Fruit

Single wounds were made with a nail on the equator of apples, cv Gala, which were placed in plastic plates, wounded side up, in 3.8 L plastic boxes. Nine apples were placed in each box and there were three boxes per treatment. The fruits were inoculated with blue mold, *Penicillium expansum* by pipetting 20 μl of conidial suspension ($10^4$/ml) into each wound either 24 hours before (pre-inoculation) or immediately before the experiment. For the *Muscodor* fumigation treatment, 140 grams of colonized rye grain were placed in the containers which were then sealed. The control contained only inoculated fruits in sealed boxes. They were incubated at room temperature (19–22° C.). Disease was evaluated as the percentage of infected fruits after 7, 14 and 21 days (Table 3). The treatment that was pre-inoculated showed no infection of the apples while a very low infection rate was seen of only 7% at the 21 day rating for fruit inoculated immediately before exposing the fruit to *Muscodor*.

Example 13

Activity of *Muscodor albus* Against Insects and Nematodes

Nematode (*Caenorhabditis elegans*)

Plates using the moat system (Worapong et al., 2001) were inoculated on one side with *M. albus*, and on the opposite side with *E. coli*, or free-living nematodes with *E. coli*. Identical plates were set up without the *Muscodor*. After five-days the plate without the *Muscodor* had developed a large reproducing population of nematodes which crossed the moat and were beginning to populate the opposite side of the petri dish. The *E. coli* had grown to normal colony morphology on the companion plate. The *Muscodor* treated plate had developed a substantial colony that was sending mycelia across the surface of the PDA. The nematodes that were present were sluggish, yet motile. By seven days, the *Muscodor* reached the edge of the PDA and was sending mycelia into the moat of the plate with *E. coli*, and the plate with the round worms. Only a small number of living adult nematodes were present on the agar, and their mobility was limited.

Beet Armyworm (*Spodoptera exigua*)

Three small plastic beakers containing approximately 150 grams of autoclaved rye seed colonized with *M. albus* were placed in a plastic box (approximately 250 in²). A companion box was set up at room temperature with out the three beakers of fungus. Both boxes contained a petri plate of PDA with a small plug of *Rhizoctonia solani* in the center, as a bioassay indicator. 96-well microtitre plates containing beet armyworm eggs that had been overlaid onto artificial diet were introduced into each box. After two days, the eggs in the box without the *Muscodor* began to hatch, and the *R. solani* developed new mycelia. The armyworm eggs did not hatch in the box containing the rye culture of *M. albus*. Moreover, the growth of *R. solani* was suppressed. After 5 days, the armyworms in the untreated box had achieved second to third instar.

Paired microtitre plates were introduced into the boxes with armyworms larvae that had been grown for three days on artificial diet. The plate in the *Muscodor* box ceased feeding and remained stunted compared to the untreated controls. After five days, the armyworms in the treated plate were dead.

Corn Rootworm Beetles, *Diabrotica undecimpunctata*

Paired microtitre plates were introduced into the boxes with corn rootworm eggs that had been overlaid onto artificial diet. The eggs had just begun to hatch when the plates were introduced into the test boxes. Approximately half of the eggs hatched in the *Muscodor* box. The remainder did not hatch, and all of the neonates were dead within two days. The microtitre plate in the untreated control box developed a normal infestation that progressed with 3–6 third-instar grubs per well, after one-week.

Example 14

Treatment of Smut Infested Barley Seeds with *Muscodor albus*

In controlled, replicated experiments, 25 barley seeds infested with *Ustilago hordei* (covered smut, Table 6) were placed in each of two agar plates with the gases of *M. albus* for four days and then planted in test pots in the greenhouse. After 15 weeks the plants were harvested and evaluated for smut in the seed heads. There was 100% control of this disease in two groups of plants that had been exposed to *M. albus* gases and no sign of any inhibition or damage to the plants caused by the gas treatment. An identical number of control plants (untreated and *U. hordei* infested seed) had 50% and 41%, respectively of infected seed heads in this experiment. Also, as expected, uninfected seed yielded plants having no diseased grains.

Results and Discussion

*Muscodor albus*, gen. et sp. nov., is a deuteromycetous (mycelial sterilia) endophytic species bearing molecular relatedness to the ascomyceteous group-*Xylaria*. The fungus is related to *Xylariaceae* by virtue of 96–98% homology of its 18S rDNA (2089 bp) to representative members of this group. Furthermore, ITS1, 5.8S, and ITS2 sequences (652 bp) of *M. albus* showed close relatedness to several *Xylaria* spp. including *X. arbuscula, X. longipes,* and *X. mali* at the 89–92% level. Both the 18S rDNA and the ITS 1&2 5.8 S rDNA are unique, and therefore, *Muscodor* is considered a taxonomically distinct genus and species. (Worapong et al., 2001)

The volatiles of *M. albus* were also tested against plants inoculated with pathogenic fungi. The volatiles themselves had no detrimental effects on higher plants that were tested. However, it was possible to demonstrate a 100% control of covered smut of barley using the volatiles to treat seed inoculated with *Ustilago hordei*. Thus, because of the potential practical importance of volatile antibiotic producing fungi it was deemed important to determine if other organisms in this group exist in nature.

Using standard techniques for the isolation of endophytic fungi, as well as the use of the volatiles of *M. albus* as a selection tool in culture, at least two more volatile antibiotic producing endophytes were isolated. These organisms were obtained from two separate tree species native to Australia. These two fungal cultures bore similarities to *M. albus* in that they made no fruiting structures in culture, produced no spores, had a musty odor and were inhibitory or lethal to many microorganisms. However, by the same token, these organisms possessed cultural, chemical, and molecular biological characteristics that differed from *M. albus*.

It has been well demonstrated that the molecular characteristics of an organism are unique to it and it can be used to help in classification especially when critical structures (spore production) or other features are missing. Thus, the phylogenetic character mapping method combined with morphological data can assist in fungal identification. Commonly, the rDNA genes are targeted for taxonomic purposes because they are highly conserved (Bruns et al., 1991; Guarro et al., 1999 and Mitchell et al., 1995). In addition to its 18S rDNA, the ITS1&2 sequences are also conserved. After searching partial 18S rDNA sequences of *M. roseus* "A3-5" (2055 bp) with data in GenBank under BLASTN 2.2.1, the results showed 100% similarities with 2089 bp of *Muscodor albus* (AF324337) from site 1–981, 1319–2048, and 98% similarities with 982 bp of *Xylaria polymorpha* (AB014043) and *Hypoxylon fragiforme* (AB014046), and 97% similarities with 982 bp of *Rosellinia necatrix* (AB014044). In addition, isolate "A-10" possesses 99% sequence similarity of its 18Sr DNA (2051 bp) to that of isolate "A3-5."

On the other hand, comparative analysis of the ITS 1&2 and 5.8S rDNA sequences of *M. roseus* "A3-5" hit ITS 1&2 of *Muscodor albus* (AF324337), *X. arbuscula* CBS 452.63 (AF163029) and CBS 454.63 (AF163028), *X. enteroleuca* CBS 148. (AF163033), *X. longipes* CBS 148.73 (AF163038), *X. mali* CBS 385.35 (AF163040), *X. cornudamae* CBS 724.69 (AF163031), at 99, 91, 91, 91, 90 and 89% similarities, respectively. No total identities of either partial 18S rDNA or ITS 1&2 and 5.8S rDNA sequences were found.

Phylogenetic analysis based on 18S sequences showed that *M. roseus* is a sister group to *Muscodor albus* (AF324337) with robust bootstrap confidence measured 100% from 100 replications. In addition, maximum parsimony analysis shows that both *M. albus* and *M. roseus* are more closely related to the *Xylariaceae* e.g. *Xylaria* spp., *Rosellinia necatrix* (AB014044) and *Poronia punctata* (AF064052) than to three representative genera of *Amphishaeriaceae: Pestalosphaeria hansenii* (AF242846), *Discostroma tricellular* (AF346546) and *Amphisphaeria* sp. (AF346545) with bootstrap confidence measured at 68% from 100 replications (Felsenstein, 1985). This result was also supported by a strict consensus heuristic search phylogenic tree of 30 equally most parsimonious 18s rDNA cladograms. Therefore, *M. roseus* should be placed in the family *Xylariaceae, Xylariales*. Moreover, the results of the comparison both the 18S rDNA and the ITS 1&2 and 5.8S rDNA of *M. roseus* "A3-5" possess high similarities to *M. albus* (Worapong et al., 2001). Also, the molecular biological data (18Sr DNA) suggests that bothisolates "A3-5" and "A-10" of *M. roseus* should be considered closely related, and virtually identical organisms. Furthermore, the molecular biological data provides some support of the concept for the division of *M. albus*, previously described, from this proposed new fungal species—*M. roseus*.

While the molecular biology of *M. roseus* shows that this organism has the best fit into the group—Xylariaceae, it also demonstrates close 18Sr DNA relatedness to *M. albus*. However, because there is such relatedness at the limited r-DNA molecular level, it may be argued that the two fungi are identical. Nevertheless, other chemical characters in both *M. albus* and *M. roseus* were examined and discovered to be different. Thus, while both *M. albus* and *M. roseus* shared the biochemical ability of producing a musty smelling odor, which has been demonstrated to have powerful antibiotic properties, many of the volatiles produced by these two organisms were identical as measured by GC/MS. It has been often noted that fungi do produce a variety of odorous substances, but the impressive antibiotic properties of *Muscodor* spp. seems to be unique (Bjurman et al., 1992; Rapoir et al., 2000 and Schnurer et al., 1999). However, the volatiles of these two fungi also contained different compounds (Strobel et al., 2001). As an example, *M. albus* produced 2-nonanone, caryophyllene, and acetic acid 2-phenylethyl ester, while these compounds were not detected in either isolate of *M. roseus*. On the other hand, bothisolates of *M. roseus* made compounds not detected in *M. albus* volatiles, such as 2-butenoic acid, ethyl ester; 1,2,4, trimethyl benzene and 2,3 nonadiene. This result lends some chemical support to the assignment given in this report suggesting that *M. albus* is taxonomically distinct from *M. roseus*.

Other, more classical features of *M. roseus* (isolates "A3-5" and "A-10") were also examined and compared to *M. albus*. These isolates of *M. roseus* produced a slow growing, dense, lightly rose colored mycelium on all media tested. This contrasts to *M. albus* that produces a whitish mycelium on all comparable media tested (Worapong et al., 2001). No spores formed on any medium including ones containing the host plant material or carnation leaves. Hyphae varied in diameter (0.8–3.6 μm) and were often intertwined to make more complex structures and even hyphal coils. These hyphae were generally bigger than those of *M. albus*. The mycelia of *M. roseus* generally make more complex interwined structures in culture than *M. albus*. In fact, the appearance of hyphal coils of fungi in culture is not common, in our experience, and yet these structures often appeared in *M. roseus* cultures.

Finally it is to be noted that for *M. roseus*, the best storage condition was after drying on filter paper and placement at −70° C. Under these conditions the fungus remains vailable for over 1.5 years. Also, this fungus could be stored at 4° C. in sterile water but with less certainty of recovering a viable organism after 6 months. Also, storage in 15% glycerol at −70° C. effectively preserved the viability of the organism.

The preceding discussion and examples are intended merely to illustrate the art. As is apparent to one of skill in the art, various modifications can be made to the above without departing from the spirit and scope of this invention.

References

1. Altschul, S. F., et al. (1997). Nucleic Acids Res. 25: 3389–3402
2. Bacon C. W. and White JR. J. F. Microbial Endophytes. Marcel Dekker Inc., New York. .
3. Bjurman J. and Kristensson, J. (1 992) Mycopathologia 118: 173.
4. Bruns, T. D., et al. (1991). Annu. Rev. Ecol. Syst. 22: 525–564.
5. Dennis, C. & Webster, J. (1971) Trans. Br. Mycol. Soc. 57: 41–48
6. Felsenstein, J. (1985). Evolution 39: 783–791.
7. Guarro, J., et al. (1999). Clinical Microbiology Reviews, 12: 454–500.
8. Hawksworth, D. C. and Rossman, A. Y. (1987) Phytopath. 87: 888.
9. Heathcock, R. and Ratcliffe, R. (1971). J. Am. Chem. Soc. 93: 1746.
10. Hoefle, G. et al., (1978) Vorbrueggen, Agnew. Chem., Int. Ed. Engl. 17: 569.
11. Lee, S. B. and Taylor, J. W. (1990). In *PCR Protocols* A Guide to Methods and Applications. Edited by Innis, M. A., Gelfand, D. H., Sninsky J. J., White, T. J. Academic Press, Inc., California: pp. 282–287.
12. Li, J. Y. et al., (2000), Org. Lett. 2: 767.
13. Li, J. Y. et al., (2001), Phytochem. 56: 463.
14. Mitchell, J. I., et al. (1995). Mycologist 9: 67–75.
15. Nelson, P. V.(1998) Greenhouse Operation and Management 5$^{th}$ ed. Prentice-Hall.
16. Rapior, S., et al. (1995). Mycologia 92: 305–308.
17. Rapior, S. (2000), Mycologia 92: 305.
18. Schnürer, J., et al. (1999). Fungal Genetics and Biology 27: 209–217.
19. Schnurer, J. et al., (1999), Fungal Genetics and Biology 27: 209.
20. Stierle, A. et al., (1993), Science 260: 214.
21. Strobel, G. A. et al., (2001), Microbiol. 147: 2943–2950.
22. Strobel, G. A., et al. (1996). Microbiology 142: 435–440.
23. Strobel, G. A., et al. (2000). Mycotaxon. 76: 257–266.
24. Swofford, D. L. (1999). Phylogenetic Analysis Using parsimony (* and Other Methods). Version 4.0d64. Sunderland, Mass.: Sinauer Associates.
25. Thomson, J. and Gibson T. (1997). Clustal V. Multiple Sequence Alignments. In: Documentation (Installation and Usage) European Molecular Biology Laboratory Postfach Germany: 1–37.
26. White, T. J., et al. (1990). Amplification and direct sequencing of fungal ribosomal RNA genes for phylogenetics. In *PCR Protocols*: A guide to Methods and Applications. Edited by Innis, M. A., Gelfand, D. H., Sninsky J. J., White, T. J. Academic Press, Inc., California: 315–324.
27. Willits, D. A. and Sherwood, J. E. (1999). Phytopath. 89: 212–217.
28. Worapong, J. et al. (2001). Mycotaxon. 79: 67–69.
29. Yang, X. et al., (1994), Plant Science 102:1.

TABLE 1

The effects of the volatile compounds of *M. albus* and an artificial mixture of *M. albus* compounds on a group of test microbes.

| Test Microbe | % Growth over control after a 2 day exposure to *M. albus* | Viability after 3 days exposure to *M. albus* culture | $IC_{50}$ in artificial atmosphere for 2 days (μl/CC) | % Growth (mm) over control in artificial atmosphere | Viability after 3 days exposure artificial atmosphere |
|---|---|---|---|---|---|
| *Pythium ultimum* | 0 | Dead | 0.48 ± 0.01 | 0 | Dead |
| *Phytophthora cinnamoni* | 0 | Dead | 0.29 ± 0.06 | 0 | Dead |

TABLE 1-continued

The effects of the volatile compounds of *M. albus* and an artificial mixture of *M. albus* compounds on a group of test microbes.

| Test Microbe | % Growth over control after a 2 day exposure to *M. albus* | Viability after 3 days exposure to *M. albus* culture | $IC_{50}$ in artificial atmosphere for 2 days ($\mu$l/CC) | % Growth (mm) over control in artificial atmosphere | Viability after 3 days exposure artificial atmosphere |
|---|---|---|---|---|---|
| *Penicillium expansum* | 0 | Dead | # | # | # |
| *Rhizoctonia solani* | 0 | Dead | 0.08 ± 0.02 | 0 | Dead |
| *Ustilago hordei* | 0 | Dead | 0.31 ± 0.09 | 0 | Dead |
| *Stagnospora nodorum* | 0 | Dead | 0.15 ± 0 | 0 | Dead |
| *Sclerotinia sclerotiorum* | 0 | Dead | 0.17 ± 0.05 | 0 | Alive |
| *Scerotinia minor* | 0 | Dead | # | # | # |
| *Aspergillus fumigatius* | 0 | Dead | 0.41 ± 0.05 | 0 | Alive |
| *Monilinia fructicola* | 0 | Dead | # | # | # |
| *Fusarium solani* | 19.4 ± 0.284 | Alive | 1.13 ± 0.07 | 42.0 ± 2 | Alive |
| *Fusarium oxysporum* | 4 | Alive | # | # | # |
| *Verticillum dahliae* | 0 | Dead | 0.3 ± 0 | 0 | Dead |
| *Cercospora beticola* | 17.5 ± 3.5 | Alive | 0.12 ± 0.15 | 8 ± 2 | Alive |
| *Tapesia yallundae* | 0 | Dead | 0.64 ± 0 | 0 | Dead |
| *Xylaria* sp. | 25 ± 0 | Alive | 0.41 ± 0.03 | 0 | Alive |
| *Muscodor albus* | 100 ± 0 | Alive | 0.6 ± 0 | 17.5 ± 7.5 | Alive |
| *Escherichia coli* | 0 | Dead | # | 0 | Dead |
| *Staphlococcus aureus* | 0 | Dead | # | 0 | Dead |
| *Micrococcus luteus* | 0 | Dead | # | 0 | Dead |
| *Candida albicans* | 0 | Dead | # | Trace | Alive |
| *Bacillussubtilus* | 0 | Alive | # | 0 | Alive |

Legend:
*The amount of each positively identified compound used in the artificial mixture was obtained by applying the electron ionization cross section (% of the total area) of the compound obtained in the GC/MS analysis.
The artificial mixtures were subsequently tested by placing them in a pre-sterilized microcup (4 × 6 mm) located in the center of a test Petri plate containing PDA.
Agar plugs containing freshly growing test microbes (or streaked microbes) were positioned about 2–3 cm from the center microcup.
Then the plate was wrapped with 2 layers of parafilm and incubated for two or more days at 23° C..
Measurements of linear mycelial growth were made from the edge of the inoculum agar plug to the edge of the mycelial colony.
Not measured in this experimental design.

TABLE 2

Average number of broccoli seedlings per pot one week after planting (means + standard deviation) using vermiculite.

| Muscodor treatment | Non-infested | Rhizoctonia-infested |
|---|---|---|
| Unsealed pots | | |
| Check | 65 ± 1 | 1 ± 1 |
| Liquid: 50 ml/L | 64 ± 11 | 39 ± 11 |
| Liquid: 200 ml/L | 61 ± 8 | 63 ± 15 |
| PDA culture | 62 ± 5 | 68 ± 1 |
| Sealed pots | | |
| Check | 65 ± 1 | 1 ± 1 |
| Liquid: 50 ml/L | 59 ± 3 | 31 ± 19 |
| Liquid: 200 ml/L | 57 ± 2 | 66 ± 11 |
| PDA culture | 62 ± 6 | 62 ± 10 |

TABLE 3

Percent of applies infected with blue mold (*Penicillium expansum*) after 7, 14 and 21 days, comparing pre-inoculation with blue mold to inoculation immediately before exposure to Muscodor. Untreated controls were not exposed to Muscodor.

| Treatments | 7 days | 14 days | 21 days |
|---|---|---|---|
| Untreated Control | 100 | 100 | 100 |
| Muscodor | 0 | 0 | 7 + 13 |
| 24 hour pre-inoc | | | |
| Untreated Control | 100 | 100 | 100 |
| Muscodor | 0 | 0 | 0 | a: standard deviations are high due to small number of fruits.

TABLE 4

GC/MS analysis of the volatile compounds produced by *M. albus*.

| RT | Total Area (%) | M/z | Possible compound | MW |
|---|---|---|---|---|
| 3:45 | 0.33 | 114 | Octane | 114 |
| 4:19 | 0.93 | 58 | Acetone | 58 |
| 4:37 | 0.68 | 74 | Methyl acetate | 74 |
| 5:56 | 7.63 | 88 | Ethyl acetate | 88 |
| 6:51 | 0.31 | 102 | Propanoic acid, 2-methyl, methyl ester | 102 |
| 7:16 | 6.24 | * | Ethanol | 46 |
| 8:03 | 2.07 | 116 | Propanoic acid, 2-methy-methyl ester | 116 |
| 11:45 | 0.58 | * | Propanoic acid, 2-methyl 2-methylpropyl ester | 144 |
| 12:05 | 2.06 | 74 | Isobutyl alcohol | 74 |

TABLE 4-continued

GC/MS analysis of the volatile compounds produced by *M. albus*.

| RT | Total Area (%) | M/z | Possible compound | MW |
|---|---|---|---|---|
| 12:50 | 22.24 | * | 1-butanol, 3-methyl, acetate | 130 |
| 14:57 | 1.53 | * | Propanoic acid, 2-methyl, 3-methylbutyl ester | 158 |
| 15:28 | 22.99 | * | 1-butanol, 3-methyl- | 88 |
| 16:08 | 0.29 | 138 | # Furan, 2-pentyl- | 138 |
| 18:53 | 0.29 | 142 | # 4-nonanone | 142 |
| 20:38 | 0.41 | 142 | 2-nonanone | 142 |
| 21:07 | 0.30 | 204 | # Naphthalene, decahydro-4a-methyl-1-methylene-7-(1-methylethylidene)-, (4aR-trans)- | 204 |
| 22:54 | 1.51 | 204 | # Azulene, 1,2,3,4,5,6,7,8-octahydro-1,4-dimethyl-7-(1-methylethenyl)-, [1S-(1.alpha., 4.alpha., 7.alpha.)] | 204 |
| 23:16 | 0.94 | 204 | # Cyclohexene, 4-(1,5-dimethyl-1,4-hexadienyl)-1-methyl- | 204 |
| 25:20 | 3.63 | 204 | # 1H-3a,7-methanoazulene, 2,3,4,7,8,8a-hexahydro-3,6,8,8 tetramethyl-, [3R-(3.alpha., 3a.beta., 7.beta., 8a.alpha.)] | 204 |
| 25:30 | 6.08 | 88 | Propanoic acid, 2-methyl | 88 |
| 26:04 | 0.48 | 204 | Caryophyllene | 204 |
| 27:55 | 0.34 | 204 | # Naphthalene, 1,2,4a,5,6,8a-hexahydro-4,7-dimethyl-1-(1-methylethyl)-, [1R-(1.alpha., 4a.alpha., 8a.alpha.)] | 204 |
| 28:34 | 0.36 | 204 | # Spiro[5.5]undec-2-ene, 3,7,7-trimethyl-11-methylene | 204 |
| 28:50 | 1.07 | 204 | Azulene, 1,2,3,5,6,7,8,8a-octahydro-1,4-dimethyl-7-(1-methylethyenyl)-, [1S-(1.alpha., 7.alpha., 8a.beta.)] Common Name: Bulnesene | 204 |
| 28:57 | 3.24 | 204 | Naphthalene, 1,2,3,5,6,7,8,8a-octahydro-1,8a-dimethyl-7-(1-methylethenyl)-, [1R-(1.alpha., 7.beta., 8a.alpha.)] Common Name: Valencene | 204 |
| 31:12 | 1.74 | * | Acetic acid, 2-phenylethyl ester | 164 |
| 33:17 | 1.06 | 122 | Phenylethyl alcohol | 122 |
| 39:00 | 9.76 | 204 | Unknown | 204 |

\* No molecular-ion peak was observed in the spectrum of either the standard compound or the compound undergoing the analysis.

Denotes that a spectrum and retention time of this component was observed and the substance matched to the most likely compound in the NIST data base, but the data have not been confirmed by use of an appropriate identical standard compound by either retention time or MS. These compounds were not placed in the artifical mixture in the bioassay test.

TABLE 5

The inhibitory influence of each class of volatile compounds is expressed as the % of the test microbe growth as compared to a control not in the presence of the test compounds.

| Test Microbe # | Alcohols 0.48 µl/cc % growth of control | Esters 0.53 µl/cc % growth of control | Ketones 0.02 µl/cc % growth of control | Acids 0.09 µl/cc % growth of control | Lipids 0.08 µl/cc % growth of control |
|---|---|---|---|---|---|
| *Pythium ultimum* | 11.2 ± 4 | 0 | 67.5 ± 7 | 40.9 ± 3 | 75 ± 0 |
| *Rhizoctonia solani* | 55 ± 5 | 0 | 67.5 ± 7.5 | 67.5 ± 7.5 | 40 ± 0 |
| *Tapesia yallundae* | 35 ± 15 | 0 | 75 ± 25 | 100 ± 0 | 100 ± 0 |
| *Xylaria* sp. | 75 ± 25 | 0 | 100 ± 0 | 100 ± 0 | 100 ± 0 |
| *Sclerotinia sclerotiorum* | 29 ± 3 | 8.1 ± 1.5 | 20.6 ± 12 | 40 ± 0 | 78 ± 2 |
| *Cercospora beticola* | 58 ± 8 | 5 ± 5 | 100 ± 0 | 83 ± 17 | 100 ± 0 |
| *Fusarium solani* | 70 ± 10 | 55 ± 5 | 90 ± 10 | 80 ± 20 | 80 ± 10 |

\*All measurements of mycelial growth compared to the untreated control were made as described in Table 1.
None of the microbes were killed after a three day exposure to any of the artificial test mixtures given on this table.

TABLE 6

Number of Barley Seeds Heads Infected within *Ustilago hordei* with and without *Muscodor albus* Pre-treatment.

| Treatment | Ratio of Diseased to Healthy Plants | |
|---|---|---|
| | Expt 1 | Expt 2 |
| No treatment | 16/32 | 13/31 |
| *M. albus* volatiles | 0/33 | 0/42 |
| Uninfested control | 0/41 | 0/39 |

What is claimed is:

1. A biologically pure culture of a strain of *Muscodor*.

2. A biologically pure culture of a strain of *Muscodor albus*.

3. A biologically pure culture of a strain of *Muscodor roseus*.

4. A composition comprising the biologically pure culture of any one of claims 1–3 and a carrier.

5. The composition of claim 4, wherein the carrier is an agriculturally acceptable carrier.

6. The composition of claim 4, further comprising at least one chemical or biological pesticide.

7. The biologically pure culture of claim 2 wherein the strain is NRRL 30547.

8. The biologically pure culture of claim 3 wherein the strain is NRRL 30548.

* * * * *